(12) United States Patent
Döring et al.

(10) Patent No.: US 7,560,550 B2
(45) Date of Patent: Jul. 14, 2009

(54) METHOD FOR THE PRODUCTION OF OH PROTECTED[4-(2.6-DIAMINO-9H-PURINE-9-YL)-1.3-DIOXOLANE-2-YL]METHANOL DERIVATIVES

(75) Inventors: Wolfgang Döring, Mehring (DE); Hermann Petersen, Burghausen (DE)

(73) Assignee: RFS Pharma, LLC, Tucker, GA (US)

( * ) Notice: Subject to any disclaimer, the term of this patent is extended or adjusted under 35 U.S.C. 154(b) by 401 days.

(21) Appl. No.: 10/595,067

(22) PCT Filed: Jul. 22, 2004

(86) PCT No.: PCT/EP2004/008197

§ 371 (c)(1),
(2), (4) Date: Jan. 27, 2006

(87) PCT Pub. No.: WO2005/012302

PCT Pub. Date: Feb. 10, 2005

(65) Prior Publication Data

US 2006/0211855 A1 Sep. 21, 2006

(30) Foreign Application Priority Data

Jul. 31, 2003 (DE) ................. 103 35 061

(51) Int. Cl.
*C07F 7/18* (2006.01)
*C07D 473/16* (2006.01)

(52) U.S. Cl. ....................... 544/229; 544/277

(58) Field of Classification Search ................. 544/229, 544/277

See application file for complete search history.

(56) References Cited

U.S. PATENT DOCUMENTS

| 5,179,104 A * | 1/1993 | Chu et al. .................... 544/310 |
| 6,541,625 B2 * | 4/2003 | Cimpoia et al. .......... 536/27.14 |
| 7,122,693 B2 * | 10/2006 | Belleau et al. ............... 558/252 |

FOREIGN PATENT DOCUMENTS

| EP | 1 258 486 A2 | 11/2002 |
| WO | WO 92/14729 A1 | 9/1992 |
| WO | WO 97/21706 A1 | 6/1997 |
| WO | WO0047759 A1 * | 8/2000 |
| WO | WO 01/58894 A1 | 8/2001 |

OTHER PUBLICATIONS

Robert A. McClelland and N. Esther Seaman. Can. J. Chem. 62, 1608 (1984).*
Greene and Wuts, Protective Groups in Organic Synthesis (Third Edition), John Wley & Sonce, Inc., 1999, pp. 573-575.*
Kim et al., "1,3-Dioxolanylpurine Nucleosides (2R, 4R) and (2R, 4S) with Selective Anti-HIV-1 Activity in Human Lymphocytes," J. Med. Chem., vol. 36, 1993, pp. 30-37.
Evans et al., "Divergent Asymmetric Syntheses of Dioxolane Nucleoside Analogues," Tetrahedron: Assymmetry, vol. 4, No. 11, 1993, pp. 2319-2322.
Kim et al., "L-β-(2S, 4S)- and L-α-(2S, 4R)-Dioxolanyl Nucleosides as Potential Anti-HIV Agents: Asymmetric Synthesis and Structure-Activity Relationships," Journal of Medicinal Chemistry, vol. 36, No. 5, Mar. 1993, pp. 519-528.
Vobrüggen et al., "On the Mechanism of Nucleoside Synthesis," Chem. Ber. 114, 1981, pp. 1256-1268.
March et al., "Advanced Organic Chemistry," Wiley & Sons, Inc., 3$^{rd}$ Edition, p. 179 and pp. 310-317, 1985.
Greene et al., "Protection for the Hydroxyl Group Including 1,2- and 1,3-Diols," Protective Groups in Organic Synthesis, John Wiley & Sons, Inc., 2$^{nd}$ Edition, pp. 10-117, 1991.
"Protection for the Amino Group," Protective Groups in Organic Synthesis, John Wiley & Sons, Inc., 2$^{nd}$ Edition, pp. 309-385, (Greene et al., 1991).

* cited by examiner

*Primary Examiner*—Mark L Berch
(74) *Attorney, Agent, or Firm*—David Bradin; Intellectual Property/Technology Law

(57) ABSTRACT

Glycosylation of 2,6-diaminopurines or silyl derivatives thereof with a compound of the structure

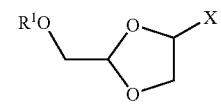

is facilitated by the presence of an optionally silylated 1,3-dicarbonyl compound during glycosylation. Byproducts are minimized, while stereoselectivity may be altered by choice of Lewis acid and other reaction condictions.

18 Claims, No Drawings

METHOD FOR THE PRODUCTION OF OH PROTECTED[4-(2.6-DIAMINO-9H-PURINE-9-YL)-1.3-DIOXOLANE-2-YL]METHANOL DERIVATIVES

CROSS-REFERENCE TO RELATED APPLICATION

This application is the U.S. national phase of PCT Appln. No. PCT/EP2004/008197 filed Jul. 22, 2004, which claims priority to German application 103 35 061.6, Filed Jul. 31, 2003.

BACKGROUND OF THE INVENTION

1. Field of the Invention

The invention relates to a method for the production of [4-(2,6-diamino-9H-purin-9-yl)-1,3-dioxolan-2-yl]methanol derivatives comprising a protective group $R^1$ on the hydroxyl group (abbreviated below to hydroxyl protective group or "OH-protected") of the general formula (1), where the radicals $R^8$, $R^9$, $R^{10}$ and $R^{11}$ are independently of one another hydrogen or an amino protective group.

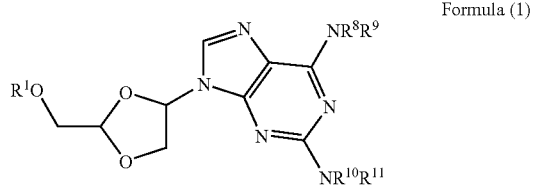

Formula (1)

2. Description of the Related Art

Nucleosides and nucleoside analogs represent an important class of substances having antiviral activity. Examples of nucleoside analogs showing activity against HIV are 3'-azido-3'-deoxythymidine (AZT) and 2',3'-dideoxycytidine (ddC). Because of various effects, but especially because of the occurrence of resistances, more modern substances with a modified profile of action have been developed.

The nucleoside analogs which have proved to be particularly advantageous are those comprising a 1,3-oxathiolane ring such as, for example, lamivudine (3TC) and coviracil (FTC) or a 1,3-dioxolane ring such as [(2R,4R)-[4-(2,6-diamino-9H-purin-9-yl)-1,3-dioxolan-2-yl]methanol (abbreviated below to "(−)-DAPD").

The synthesis of such nucleoside analogs by reacting the nucleobase or its synthetic precursor with the sugar unit in the presence of a Lewis acid now represents a standard reaction known in the art. If a silylated nucleobase is used therein, the reaction is known as the "silyl Hilbert-Johnson reaction" [H. Vorbrüggen, G. Hoefle, Chem. Ber. 1981, 114, 1256-1268].

Lewis acids frequently used, in addition to metal halides and alcoholates, and transition metal halides and alcoholates such as $SnCl_4$, $TiCl_4$ or $TiCl_2(OiPr)_2$, are silyl derivatives of perfluoro sulfonic acids such as trimethylsilyl trifluoromethanesulfonate or triakylsilyl halides such as iodotrimethylsilane.

It is assumed that the mechanism in the case of ribose derivatives (i.e. 2'-substituted sugar units) involves the formation of a cation from the sugar unit comprising a leaving group in position 1', for example, acetate, by the neighboring group effect under the influence of the Lewis acid, the cation reacting in the second step with the silylated nucleobase. In the case of silyl halides such as iodotrimethylsilane, WO 01/58894 postulates initial replacement of the leaving group by halide, for example, iodide. The iodine compound which is formed is then reacted with the silylated nucleobase.

Nucleoside analogs comprising 2,6-diaminopurine as base are normally synthesized by initially introducing 2,6-dichloropurine or 2-amino-6-chloropurine as base precursor, and the chlorine atom(s) being converted into amino groups in a later step. This can take place directly by reaction with ammonia or in two steps by reaction with azide to give the diazida derivative and subsequent catalytic hydrogenation to give the diamino derivative. The direct reaction with ammonia takes place only poorly to afford very low yields. The azide variant has the disadvantage that two reaction steps are necessary. The great disadvantage of both methods is, however, that the use of the very costly 2,6-dichloropurine or 2-amino-6-chloropurine makes the reaction economically uninteresting. In addition, because of the higher molecular weights of the precursors it is necessary to employ in the described reaction variants about 1.25 kg of dichloropurine or 1.13 kg of aminochloropurine instead of 1 kg of diaminopurine (assuming identical yields).

WO 97/21706 describes a method for producing β-nucleoside analogs having a 1,3-dioxolane ring, where a purine or pyrimidine base is reacted at temperatures below −10° C. with a 1,3-dioxolane unit which comprises a halogen atom as leaving group. The dioxolane unit is in this case preferably prepared from the corresponding acetoxy derivative by reaction with iodotrimethylsilane or diiodosilane.

Reference is made in this connection in particular to the high stereoselection when carried out at low temperatures. This method has the disadvantage that it relies on low-temperature reactions, since particularly high stereoselectivities (β:α isomer ratio) are described at a reaction temperature of −78° C.

Use of 2,6-diaminopurine as base in this method results in only poor yields or numerous byproducts (cf. Comparative Example 5). In addition, because of the low reactivity of diaminopurine, the low reaction temperatures which are, according to the teaching of WO 97/21706, necessary to achieve high stereoselectivities are a great technical disadvantage of the method because they necessitate very long reaction times (>24 h).

WO 01/58894 describes the production of DAPD and its enantiomers by applying the method disclosed in WO 97/21706 to the reaction of 4-acetoxy-2-benzoyloxymethyl-1,3-dioxolane with 2-amino-6-chloropurine (carried out at −15° C.). The product which has been purified by column chromatography and has a β:α isomer ratio of 2.3:1 is then converted by reaction with methanolic ammonia and subsequent column chromatography into DAPD with a β:α isomer ratio of 2:1. The disadvantage here is once again the use of costly 2-amino-6-chloropurine and the repeated employment of column chromatography.

SUMMARY OF THE INVENTION

The invention was based on the object of providing a cost-effective method which is easy to implement industrially for producing OH-protected [4-(2,6-diamino-9H-purin-9-yl)-1, 3-dioxolan-2-yl]methanol derivatives in racemic or optically pure form, which is based on the direct reaction of 2,6-diaminopurine or of a mono- or polysilylated 2,6-diaminopurine or derivative thereof.

It has now been surprisingly discovered, that direct reaction of 2,6-diaminopurine or of a mono- or polysilylated 2,6-diaminopurine or derivative thereof takes place with high chemical yield and, where appropriate, high stereoselectivity, without elaborate purification steps, when at least one auxiliary in the form of a 1,3-dicarbonyl compound or of a silylated derivative of a 1,3-dicarbonyl compound is present in the reaction mixture during the glycosylation reaction.

DETAILED DESCRIPTION OF THE PREFERRED EMBODIMENT(S)

The invention relates to a method for the production of compounds of the general formula (1)

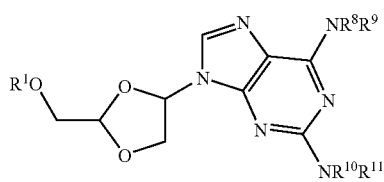

Formula (1)

where

R$^1$ is a hydroxyl protective group and

R$^8$, R$^9$, R$^{10}$, R$^{11}$ are independently of one another selected from the group comprising hydrogen or an amino protective group by reacting a compound of the general formula (2)

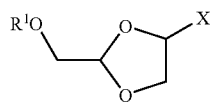

Formula (2)

where

X is a leaving group, with a 2,6-diaminopurine derivative of the general formula (5)

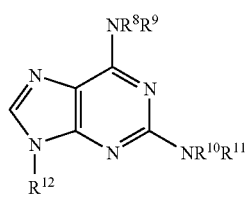

Formula (5)

where

R$^{12}$ is a silyl radical, in the presence of a Lewis acid, characterized in that a 1,3-dicarbonyl compound or a silylated derivative of a 1,3-dicarbonyl compound is additionally present.

It is possible by the method of the invention to employ cost-effective 2,6-diaminopurine derivatives directly as precursors in a reaction which can easily be implemented industrially without the need to carry out the reaction under low temperature conditions which are difficult to implement industrially, or removing unwanted byproducts from the resulting crude products by subsequent elaborate workup methods.

The method of the invention can moreover be used to produce racemic compounds of the general formula (1) and to produce optically pure products of the general formula (1) with the optical configurations of the general formulae (1a), (1b), (1c) and (1d).

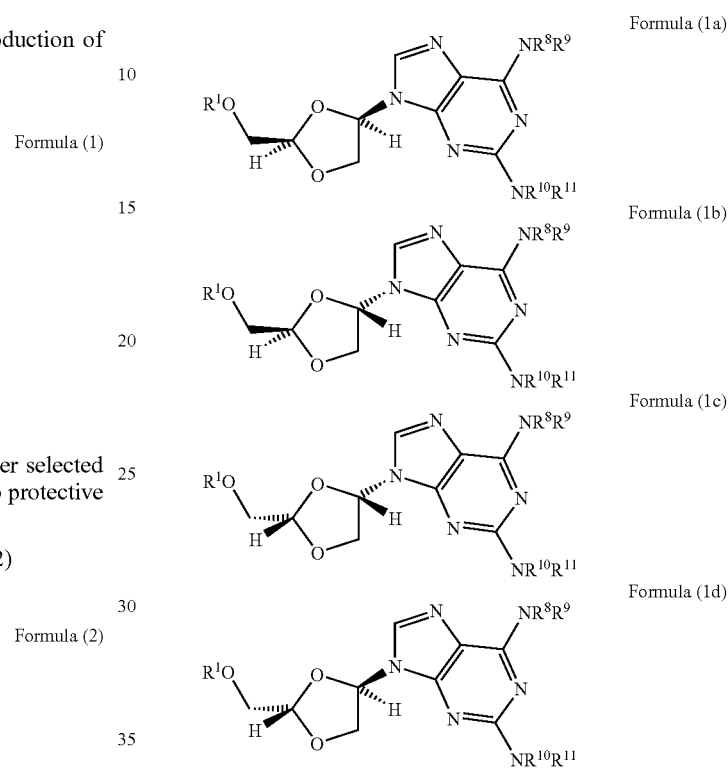

The method can be carried out with high stereoselectivity through the choice of precursors having an appropriate optical configuration.

The method of the invention is particularly suitable for producing products having the optical configuration of the general formula (1a).

The hydroxyl protective group R$^1$ can in this connection be selected from all OH protective groups known and suitable to the skilled worker; a selection of suitable OH protective groups is described in particular in T. W. Greene, P. G. M. Wuts, "Protective Groups in Organic Synthesis", 2$^{nd}$ edition, Wiley 1991, pp. 10-117.

The hydroxyl protective groups R$^1$ are preferably selected from the group comprising acyl radicals, alkyl radicals, alkoxyalkyl radicals, arylalkyl radicals, arylalkoxyalkyl radicals or silyl radicals.

Acyl radicals for R$^1$ are moreover preferably derived from an aromatic or aliphatic carboxylic acid having from 2 to 20 C atoms, particularly preferably from the group comprising benzoyl-, n-butyryl-, isobutyryl-(2-methylpropionyl-), pivaloyl-, propionyl- and acetyl-radicals.

Alkyl radicals for R$^1$ preferably consist of from 1 to 20 C atoms, with particular preference for radicals from the group comprising methyl-, ethyl- and propyl-radicals.

Alkoxyalkyl radicals for R$^1$ preferably consist of from 1 to 20 C atoms, with particular preference for radicals from the group comprising methoxymethyl-, 1-ethoxyethyl- and 2-methoxyethoxymethyl-radicals.

Arylalkyl radicals for $R^1$ preferably consist of from 1 to 20 C atoms, with particular preference for radicals from the group comprising benzyl-, 4-methoxybenzyl- and triphenylmethyl-radicals.

Arylalkoxyalkyl radicals for $R^1$ moreover preferably consist of from 1 to 20 C atoms, with particular preference for radicals from the group comprising benzyloxymethyl- and 4-methoxybeazyloxymethyl-radicals.

Silyl radicals for $R^1$ may comprise on the Si atom generally aliphatic and/or aromatic substituents having in each case from 1 to 20 C atoms, in particular having in each case from 1 to 10 C atoms. Preferred radicals are those from the group comprising trimethylsilyl-, triethylsilyl-, triisopropylsilyl-, tert-butyldimethylsilyl- and tert-butyldiphenylsilyl-radicals.

The leaving group X is defined according to J. March, "Advanced Organic Chemistry", $3^{rd}$ edition, Wiley 1985, pp. 179 and 310 et seq. as part of a substrate molecule which is eliminated during a reaction. A leaving group that carries away the electron pair of the cleaved bond is called a nucleofuge.

Leaving groups X are preferably selected from the group comprising halogen, acyloxy radical, alkylsulfonyloxy radical, arylsulfonyloxy radical, alkoxy radical or aryloxy radical.

Halogens for X are preferably iodine or bromine, with particular preference for iodine.

Acyloxy radicals for X moreover preferably consist of from 1 to 20 C atoms, with particular preference for radicals from the group comprising acetoxy-, benzoyloxy-, propionyloxy-, n-butyryloxy- and trifluoroacetoxy-radicals. Acetoxy is very particularly preferred.

Alkylsulfonyloxy radicals for X moreover preferably consist of from 1 to 20 C atoms, with particular preference for radicals from the group comprising methanesulfonyloxy-, trifluoromethanesulfonyloxy- and nonafluorobutylsulfonyloxy-radicals.

Arylsulfonyloxy radicals for X moreover preferably consist of from 1 to 20 C atoms, with particular preference for radicals from the group comprising p-toluenesulfonyloxy- (tosyl-), p-bromobeuzenesulfonyloxy- and p-nitrobenzenesulfonyloxy-radicals.

Alkoxy radicals for X moreover preferably consist of from 1 to 20 C atoms, with particular preference for radicals from the group comprising methoxy- and ethoxy-radicals.

Aryloxy radicals for X moreover particularly preferably consist of from 1 to 20 C atoms, with particular preference for radicals from the group comprising phenoxy-, 4-nitrophenoxy- and 2,4,6-trinitrophenoxy-radicals.

The 2,6-diaminopurine derivative of the general formula (5) which is employed as precursor comprises at least one silyl radical $R^{12}$ on the nitrogen atom in position 9, and optionally further silyl radicals on the two amino functions in positions 2 and 6, which in one possible embodiment are introduced in one reaction step together with the silyl group $R^{12}$ on the nitrogen atom in position 9 and, during the further reaction according to the method of the invention, act as amino protective groups for the two amino functions in positions 2 and 6. A persilylated precursor of the general formula (5) may in this connection comprise up to 5 identical or different silyl radicals. 2,6-Diaminopurine derivatives of the general formula (5) having one to three silyl radicals are preferred, and those having three silyl radicals are very particularly preferred, especially having a silyl radical on the nitrogen in position 9 and a silyl radical on each of the two amino functions in positions 2 and 6.

The silyl radicals for $R^{12}$ moreover usually comprise aliphatic and/or aromatic substituents each having from 1 to 20 C atoms, in particular each having from 1 to 10 C atoms, on the Si atom. Preferred radicals are those from the group comprising trimethylsilyl-, triethylsilyl-, triisopropylsilyl-, tert-butyldimethylsilyl- and tert-butyldiphenylsilyl-radicals. Trimethylsilyl is particularly preferred.

The 2,6-diaminopurine derivatives of the general formula (5) which are silylated at least on the nitrogen atom in position 9 can also be employed as free amines in relation to the amine functions in positions 2 and 6, in unprotected form or in a form in which one or both primary amino groups are protected with other amino protective groups.

The radicals $R^8$, $R^9$, $R^{10}$, $R^{11}$ may accordingly be independently of one another hydrogen or an amino protective group.

A selection of suitable amino protective groups can be found by the skilled worker in T. W. Greene, P. G. M. Wuts, "Protective Groups in Organic Synthesis", $2^{nd}$ edition, Wiley 1991, pp. 309-385. The amino protective groups preferably used in this connection are acyl radicals, acyloxycarbonyl radicals, alkyl radicals, arylalkyl radicals or silyl radicals.

Acyl radicals as amino protective group are moreover preferably derived from an aromatic or aliphatic carboxylic acid having from 2 to 20 C atoms, with particular preference for the radicals from the group comprising benzoyl-, acetyl- and formyl-radicals.

Acyloxycarbonyl radicals as amino protective group preferably have in this connection from 2 to 20 C atoms, with particular preference for radicals from the group comprising tert-butyloxycarbonyl-(BOC-), 9-fluorenylmethyloxycarbonyl-(Fmoc-) and benzyloxycarbonyl-(Z-)radicals.

Alkyl radicals as amino protective group moreover preferably consist of from 1 to 20 C atoms, with particular preference for radicals from the group comprising methyl- and allyl-radicals.

Arylalkyl radicals as amino protective group moreover preferably consist of from 1 to 20 C atoms, with particular preference for radicals from the group comprising benzyl- and 4-methoxybeuzyl-radicals.

Silyl radicals as amino protective group may in this connection comprise aliphatic and/or aromatic substituents each having from 1 to 20 C atoms, in particular each having from 1 to 10 C atoms, on the Si atom. Preferred radicals are those from the group comprising trimethylsilyl-, triethylsilyl-, triisopropylsilyl-, tert-butyldimethylsilyl- and tert-butyldiphenylsilyl-radicals. Trimethylsilyl is particularly preferred.

In a particularly preferred embodiment of the method of the invention, $R^{12}$ and in each case one radical $R^8$ or $R^9$, or $R^{10}$ or $R^{11}$, of the amino functions in positions 2 and 6 are trimethylsilyl, and the respective other radicals $R^8$ or $R^9$, or $R^{10}$ or $R^{11}$, are hydrogen.

The 1,3-dicarbonyl compound present in the reaction is preferably a β-carbonyl carboxylic ester, in particular a β-keto carboxylic ester, a 1,3-diketone or a malonic acid derivative having from 5 to 20 C atoms according to the general formula (3)

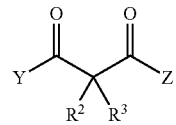

Formula (3)

or a silyl derivative of a β-carbonyl carboxylic ester, in particular of a β-keto carboxylic ester of a 1,3-diketone or of a malonic acid derivative according to the general formula (4)

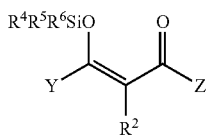

Formula (4)

where Y and Z in the general formulae (3) and the general formula 4 may be independently of one another hydrogen, an alkyl radical having from 1 to 20 C atoms, an aryl radical having from 6 to 20 C atoms or an alkyloxy group having from 1 to 20 C atoms and $R^2$ and $R^3$ in the general formula (3) may be independently of one another and $R^2$ and $R^3$ in the general formula (4) may be, independently, hydrogen, an acyl radical of an aromatic or aliphatic carboxylic acid having from 2 to 20 C atoms, an alkyl radical having from 1 to 20 C atoms or an aryl radical having from 6 to 20 C atoms and $R^4$, $R^5$ and $R^6$ in the general formula (4) may be independently of one another an aliphatic or aromatic radical having from 1 to 20 C atoms.

Particularly preferred 1,3-dicarbonyl compounds are those from the group comprising methyl glyoxylate, ethyl glyoxylate, methyl acetoacetate, ethyl acetoacetate, tert-butyl acetoacetate, isobutyl acetoacetate, isopropyl acetoacetate, n-propyl acetoacetate, benzyl acetoacetate, methyl 2-acetylacetoacetate, ethyl 2-acetylacetoacetate, tert-butyl 2-acetylacetoacetate, methyl 3-oxopentanoate, ethyl 3-oxopentanoate, tert-butyl 3-oxopentanoate, methyl 3-oxohexanoate, ethyl 3-oxohexanoate, acetylacetone, 2,4-hexanedione, 3,5-heptanedione, dimethyl malonate, diethyl malonate, diisobutyl malonate, diisopropyl malonate and di-tert-butyl malonate.

Particularly preferred silyl derivatives of 1,3-dicarbonyl compounds are those from the group comprising methyl 3-trimethylsilyloxyacrylate, ethyl 3-trimethylsilyloxyacrylate, 4-trimethylsilyloxypent-3-en-2-one, 4-triethylsilyloxypent-3-en-2-one, 4-(tert-butyldimethylsilyloxy)pent-3-en-2-one, 4-(tert-butyldiphenylsilyloxy)pent-3-en-2-one, methyl 3-trimethylsilyloxybut-2-enoate, ethyl 3-trimethylsilyloxybut-2-enoate, tert-butyl 3-trimethylsilyloxybut-2-enoate.

Preferred Lewis acids are trialkylsilyl halides and trialkylsilyl perfluoroalkanesulfonates. In this connection, iodotrimethylsilane and trimethylsilyl trifluoromethanesulfonate are particularly preferred. Iodotrimethylsilane is very particularly preferred.

Solvents which can be used are generally all aprotic organic solvents. Examples of suitable solvents are methylene chloride (dichloromethane), 1,2-dichloroethane and acetonitrile. Methylene chloride (dichloromethane) and 1,2-dichloroethane are particularly preferred. Methylene chloride (dichloromethane) is very particularly preferred.

The reaction can in principle be carried out at any temperature, which is ordinarily restricted only by the properties of the solvent and the components employed (boiling point, melting point, solubility, etc).

The reaction is preferably carried out at a temperature between −5° C. and the boiling point of the solvent used. A temperature between 0° C. and +30° C. is particularly preferably used.

The reaction is preferably carried out under atmospheric pressure.

Sugar units in the form of compounds of the general formula (2) which have proved to be particularly expedient are compounds having a leaving group X═$OCOR^7$ (acyloxy radicals), where the —$COR^7$ radical is derived from an aliphatic or aromatic carboxylic acid having from 1 to 20 C atoms, in particular acetic acid (acetoxy-), propionic acid, (propionyloxy-), n-butyric acid (n-butyryloxy-), trifluoroacetic acid (trifluoroacetoxy-) or benzoic acid (benzoyloxy-).

A number of known methods can be chosen for producing such compounds, and synthesis from 1,3-dioxolan-4-one derivatives inter alia has proved suitable.

In this connection, according to WO 92/14729 the lactone function is reduced with a selective reducing agent, and the product is reacted without isolation directly with an acylating agent such as, for example, acetic anhydride or benzoyl chloride. Examples of suitable reducing agents are diisobutylaluminum hydride (DIBAL-H) or lithium tri(tert-butoxy)aluminum hydride (LTTBA).

The compounds of the type of general formula (2) are present in the thus prepared crude products at about 40% to 70%. Byproducts and further constituents of the crude products which can in this connection be identified are inter alia 1,3-dicarbonyl compounds, especially β-keto carboxylic esters such as, for example, tert-butyl acetoacetate or isobutyl acetoacetate.

It has emerged as particularly advantageous for the starting compounds of the general formula 2 which have been prepared according to WO 92/14729 to be subjected to the silyl Hilbert-Johnson reaction without previous removal of the contained 1,3-dicarbonyl compounds from the crude products. The 1,3-dicarbonyl compounds introduced into the reaction mixture in this way can thus have the inventive effect directly when the method of the invention is carried out, the reaction of compounds of the type of general formula 2 with silylated 2,6-diaminopurine derivatives of the general formula 5 in the presence of Lewis acids.

The comparative experiment demonstrates that when 1,3-dicarbonyl compounds are removed from the precursor of the general formula (2) prepared according to WO 92/14729, for example by chromatography (Example 4), the subsequent reaction with the silylated 2,6-diaminopurine of the general formula (5) results in only a very low yield of the desired product of the general formula 1 as part of a virtually inseparable complex product mixture (Example 5).

By contrast, the desired product is obtained in a high yield and purity through the deliberate addition according to the invention of 1,3-dicarbonyl compounds or their silylated derivatives to the purified compound of the type of general formula (2).

It is possible by the method of the invention for 1,3-dicarbonyl compounds or their silylated derivatives to be introduced into the reaction mixture for the glycosylation either by deliberate addition or through the choice of an appropriate synthesis of the starting material of the general formula (2), and for the inventive effect to be achieved.

The described silyl Hilbert-Johnson reaction always results in two main products which differ in their relative stereochemistry. As already described in WO 97/21706, the stereoselectivity (cis/trans) is only very low owing to the absence of a 2' substituent (sugar numbering).

In contrast to the teaching of WO 97/21706, no dependence of the cis/trans selectivity on the reaction temperature was observable in the reaction of the invention of compounds of the type of general formula (2) with silylated 2,6-diaminopurine. The isomer ratio found when the temperature varied in a range between −78° C. and +25° C. is constant within the scope of insignificant variations.

However, surprisingly, a significant effect on the cis/trans selectivity was observable as a function of the Lewis acid used (cf. Table 2): whereas on use of iodotrimethylsilane the cis isomer usually represents the main product (cis/trans ratio between 1.5:1 and 2.5:1), the main product found on use of trimethylsilyl trifluoromethanesulfonate was the trans isomer (cis/trans ratio between 0.7:1 and 0.8:1).

The reaction mixtures after the method of the invention are expediently worked up by initial hydrolysis with water, aqueous acid or alkali. This entails hydrolysis both of the Lewis acid used and, depending on the workup conditions, where appropriate, also simultaneously of the amino protective groups of the reaction products formed, so that free amino functions result in positions 2 and 6. It is also possible to choose the hydrolysis conditions, depending on the desired final product, so that the amino protective groups are retained in positions 2 and 6.

Silyl protective groups such as, for example, trimethylsilyl-, are eliminated even with dilute acid at room temperature, whereas acyl radicals such as, for example, benzoyl- are cleaved only by heating in a basic medium or by reaction with ammonia or amines.

The hydrolytic workup is typically carried out first in an acidic pH range (pH 0 to 3). Byproducts and impurities can be removed by extraction with an organic solvent, in particular methylene chloride, 1,2-dichloroethane, toluene, hexane, heptane, THF or diethyl ether. The product is then transferred into the organic phase by adding aqueous alkali, in particular aqueous solutions of sodium hydroxide, sodium carbonate, sodium bicarbonate or potassium carbonate and renewed extraction with an organic solvent, in particular the solvents mentioned above.

After removal of the organic solvent by distillation, the product is obtained and can then be further purified where appropriate by further steps, in particular recrystallization or chromatography.

The concluding aqueous hydrolysis accordingly leads to reaction products of the general formula (1) in which the radicals $R^8$, $R^9$, $R^{10}$ and $R^{11}$ may be independently of one another hydrogen or an amino protective group, in particular to those reaction products of the general formula (1) in which all the radicals $R^8$, $R^9$, $R^{10}$ and $R^{11}$ are hydrogen.

In a preferred embodiment of the method of the invention optically pure reaction products can be prepared having the optical configurations of the general formulae (1a), (1b), (1c) and (1d), in which all the radicals $R^8$, $R^9$, $R^{10}$ and $R^{11}$ are hydrogen, by the selection of appropriately optically configured precursors. The method can be used very particularly preferably for producing products having the optical configuration of the general formula 1a in which case all the radicals $R^8$, $R^9$, $R^{10}$ and $R^{11}$ are hydrogen.

During the workup of the compounds produced by the method of the invention it is possible to achieve a further enrichment of the desired isomer (usually the cis isomer in the optical configuration of the general formulae 1a or 1c) in particular by crystallization or column chromatography. In this connection, especially when the method of the invention is implemented industrially, crystallization will be preferred for reasons of cost.

Thus, the invention further relates to a method for purifying by recrystallization the compounds of the general formula (1) obtained by the method of the invention.

Since the products of the general formula (1) are highly polar compounds having relatively high melting points, polar solvents such as alcohols, ethers or esters having 1-10 C atoms are particularly suitable for the recrystallization.

Thus, for example isopropanol is particularly preferred as solvent for the recrystallization of isobutyrates of the general formula (1) where $R^1=(H_3C)_2CHCO-$.

A single crystallization of the mixture (cis/trans~60-70:30-40) results in a product which has a cis isomer content of between 97 and 99% (cf. Example 4). It is possible by renewed recrystallization to enrich the cis isomer content to >99.5%.

The methods used to produce (non OH-protected) [4-(2,6-diamino-9H-purin-9-yl)-1,3-dioxolan-2-yl]methanol derivatives of the general formula 1 where $R^1$ is hydrogen are those familiar to the skilled worker for eliminating the appropriate OH protective group.

A selection of methods is described in particular in T. W. Greene, P. G. M. Wuts, "Protective Groups in Organic Synthesis", $2^{nd}$ edition, Wiley 1991, pp. 10-117.

Thus, the invention further relates to the use of the compounds of the general formula (1) obtained by the method of the invention for producing compounds of the general formula (6)

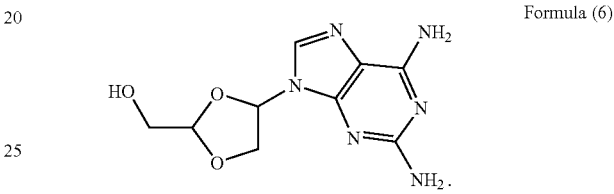

Formula (6)

This generally takes place by eliminating the hydroxyl protective groups.

In a particularly preferred variant, the compounds of the general formula (1) already employed are those in which the amino protective groups have already been eliminated by the method described above, and accordingly all the radicals $R^8$, $R^9$, $R^{10}$ and $R^{11}$ are hydrogen.

The compounds of the general formula (6) may be obtained in racemic form or in optically pure form. The products of the general formula (1) produced in optically pure form according to the invention can in particular be converted into optically pure compounds of the general formula (6).

In a particularly preferred use of the products produced according to the invention, it is possible in this way to produce (2R,4R)-[4-(2,6-diamino-9H-purin-9-yl)-1,3-dioxolan-2-yl]methanol [(−)-DAPD].

Preferred methods for eliminating acyl radicals as OH protective group are reaction with ammonia or aliphatic amines, basic aqueous hydrolysis or reaction with alcoholates such as, for example, sodium methoxide.

EXAMPLES (The Greek letter " ƺ " occurring in some examples designates a stereocenter whose absolute configuration has not been established)

Example 1

Silylation of 2,6-diaminopurine 75 g of 2,6-diaminopurine, 17.8 g of ammonium sulfate and 1451 g of hexamethyldisilazane were introduced into a 4 l three-necked flask. The suspension was heated to reflux with stirring (refluxing started at 108° C.) and kept there for 3-4 h, with the reflux temp. rising to 122° C. and the mixture becoming clear. The solution was cooled somewhat (to approx. 80° C.) and vacuum was slowly applied. The excess hexamethyldisilazane was subsequently distilled off up to a bottom temp.

of 85° C./5 mbar. GC analysis of the residue showed the following composition: 86.3% tris(trimethylsilyl)-2,6-diaminopurine, 0.5% trimethylsilyl-2,6-diaminopurine, 0.9% bis(trimethylsilyl)-2,6-diaminopurine, 10.0% bis(trimethylsilyl)sulfate, 0.3% hexamethyldisilazane. The residue was dissolved in dry methylene chloride. The amount was calculated in this case so that an approx. 1 molar solution resulted.

Example 2

Preparation of (2R-4 Ξ)-4-acetoxy-2-isobutyryloxymethyl-1,3-dioxolane

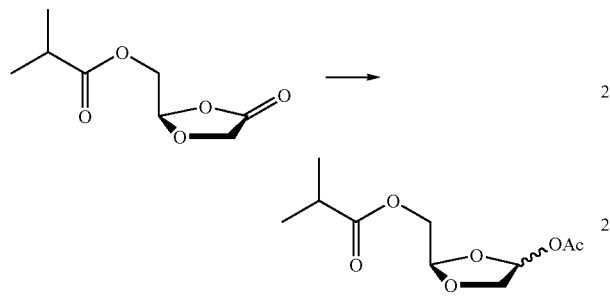

316.2 g of a 1.1 molar solution of LiAlH(OtBu)₃ in THF and 142 g of THF were introduced into a dry flask and cooled to −5° C. 53.0 g of (2R)-2-isobutyryloxymethyl-1,3-dioxolan-4-one were added dropwise over the course of 45 min. The mixture was warmed to 25° C., 33.7 g of 4-dimethylaminopyridine were added and the mixture was stirred for 1 h. It was again cooled to −5° C. and then 209 g of acetic anhydride were added dropwise at this temperature. The mixture was stirred at −5 to 0° C. for 15 h.

It was then quenched by adding 415 g of 15% strength NH₄Cl solution and diluted with 400 g of water. The THF was substantially removed by distillation in vacuo and then 480 g of ethyl acetate were added. The mixture was thoroughly shaken and the phases were separated. The aqueous phase was back-extracted once with ethyl acetate, and the combined organic phases were washed with water and NaHCO₃ solution. The solvent was distilled off in vacuo, and the product was obtained as an orange-colored liquid (yield 69.0 g with a content of 65%, corresponding to 70% of theory).

The product is obtained as cis/trans mixture with contents between 40 and 70% (GC) by this method. The cis/trans ratio is between 2.8 and 3.6. Further constituents present are, inter alia, tert-butyl acetoacetate (about 8 to about 27%) and tert-butyl 2-acetylacetoacetate (about 6% to about 15%).

Example 3

Purification of (2R-4 Ξ)-4-acetoxy-2-isobutyryloxymethyl-1,3-dioxolane by column chromatography 30 g of a product prepared as in Example 2 with a content of 42.5% were chromatographed on 200 g of silica gel (mobile phase n-heptane/ethyl acetate 4:1). The product-containing fractions were combined and the solvent was removed in vacuo. 14 g of colorless liquid were obtained. The GC content was 79.5% (yield 88%).

Example 4

Preparation of cis- and trans-(2R)-2-isobutyryloxymethyl-4-(2,6-diaminopurin-9-yl)-1,3-dioxolane

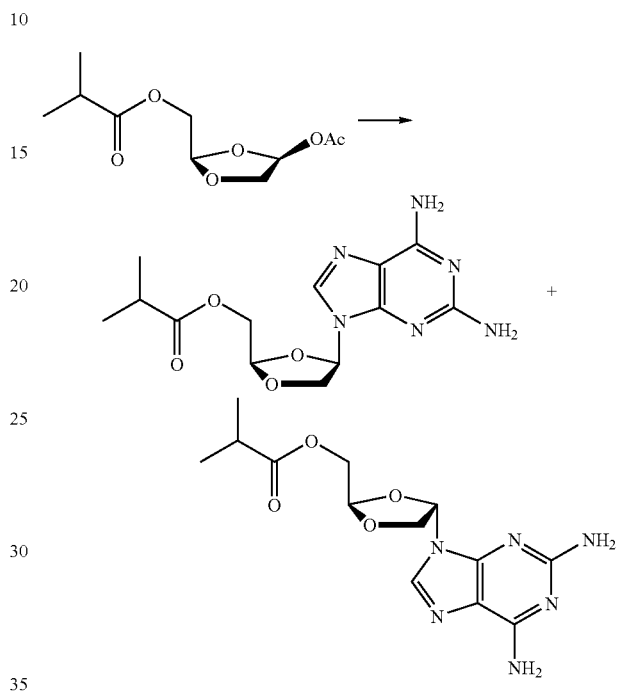

105.1 g of (2R-4 Ξ)-4-acetoxy-2-isobutyryloxymethyl-1,3-dioxolane with a content of 55.3% (13.2% tert-butyl acetoacetate and 6.3% tert-butyl 2-acetylacetoacetate; this corresponds to 0.48 mol of 1,3-dicarbonyl compound per mole of dioxolane) were introduced into 540 ml of methylene chloride. A solution of 19.8 g of tert-butyl acetoacetate in 120 ml of methylene chloride and 275 ml of a 1.0 molar solution of tris(trimethylsilyl)-2,6-diaminopurine in methylene chloride (from Example 1) were likewise added. The solution was cooled to 0° C. and, at this temperature, a solution of 125.0 g of iodotrimethylsilane (content 95.8%) in 250 ml of methylene chloride was added dropwise over the course of 20 min. The mixture was then stirred at 0° C. for 1 h, warmed to 25° C. and stirred at this temperature for 15 h. 1 l of a 10% strength Na₂CO₃ solution was added for quenching, and the mixture was stirred for 10 min. The phases were separated and the aqueous phase was back-extracted twice with methylene chloride. The combined organic phases were washed with 10% strength Na₂CO₃ solution and water and filtered through kieselguhr. The solution was then concentrated to about 1000 ml. HPLC analysis of the solution showed 67.8% cis-(2R)-2-isobutyryloxymethyl-4-(2,6-diaminopurin-9-yl)-1,3-dioxolane and 31.7% trans-(2R)-2-isobutyryloxymethyl-4-(2,6-diaminopurin-9-yl)-1,3-dioxolane (isomer ratio 2.1:1; HPLC area %). The solution was mixed with 750 ml of 0.5 N HCl and stirred for 30 min. The phases were separated and the aqueous phase was washed four times with methylene chloride.

After renewed addition of 500 ml of methylene chloride, the pH was adjusted to 8-9 by adding 10% strength Na₂CO₃ solution, and the mixture was stirred for 15 min.

The phases were separated and the aqueous phase was back-extracted with methylene chloride.

The methylene chloride was substantially distilled off, and 1 l of isopropanol was added. Distillation was continued until the distillate temperature reached 80° C. Precipitated product was dissolved by adding a further 900 ml of isopropanol at the boiling point. The solution was cooled to 25° C. over the course of 2 h and then stirred for 1 h, and the crystals which had separated out were filtered off with suction. They were then washed with isopropanol and dried in vacuo at 60° C.

35.2 g of colorless crystals which, according to NMR analysis, contained 1 mol of isopropanol in addition to (2R)-2-isobutyryloxymethyl-4-(2,6-diaminopurin-9-yl)-1,3-dioxolane. The contents by HPLC were 98.0% cis- and 1.6% trans-(2R)-2-isobutyryloxymethyl-4-(2,6-diaminopurin-9-yl)-1,3-dioxolane. This corresponds to a yield of 36.1% of cis isomer based on (2R-4 $\Xi$)-4-acetoxy-2-isobutyryloxymethyl-1,3-dioxolane.

Recrystallization from isopropanol results in pure cis isomer with a content of 99.6% (recrystallization yield 90%).

Example 5

Comparative Example 9.3 ml of a 1.0 molar solution of tris(trimethylsilyl)-2,6-diaminopurine in methylene chloride (from Example 1) were cooled to 0° C. The solution of 2.52 g of (2R-4 $\Xi$)-4-acetoxy-2-isobutyryloxymethyl-1,3-dioxolane from Example 3 with a content of 79.5% was added. At 0 to 5° C., a solution of 4.0 g of iodotrimethylsilane was added, and the mixture was then warmed to 25° C. and stirred for 15 h. It was hydrolyzed with 10% strength $Na_2CO_3$ solution. The phases were then separated and the organic phase was analyzed by HPLC.

HPLC of the organic phase showed in addition to a large number of byproducts 1.6% 2,6-diaminopurine and 34.2% cis- and 30.4% trans-(2R)-2-isobutyryloxymethyl-4-(2,6-diaminopurin-9-yl)-1,3-dioxolane.

Example 6

The procedure was analogous to Example 5 with the difference that a solution of 1.16 g of tert-butyl acetoacetate in 5 ml of methylene chloride were added before the addition of the iodotrimethylsilane.

HPLC showed no 2,6-diaminopurine and 67.8% cis- and 31.7% trans-(2R)-2-isobutyryloxymethyl-4-(2,6-diaminopurin-9-yl)-1,3-dioxolane.

Example 7

The procedure was analogous to Example 5 with the difference that a solution of 0.9 g of tert-butyl 3-trimethylsilyloxy-2-butenoate in 5 ml of methylene chloride was added before the addition of the iodotrimethylsilane.

HPLC showed 0.5% of 2,6-diaminopurine and 62.6% cis- and 33.6% trans-(2R)-2-isobutyryloxymethyl-4-(2,6-diaminopurin-9-yl)-1,3-dioxolane.

Example 8

10.3 ml of a 0.93 molar solution of tris(trimethylsilyl)-2,6-diaminopurine in methylene chloride (from Example 1) were introduced into a dry flask. 3.97 g of (2R-4 $\Xi$)-4-acetoxy-2-isobutyryloxymethyl-1,3-dioxolane (cf. Example 2) with a content of 50.4% and a content of 17.1% tert-butyl acetoacetate and 7.5% tert-butyl 2-acetylacetoacetate (this corresponds to 0.67 mol of 1,3-dicarbonyl compound per mole of dioxolane) were dissolved in 20 ml of methylene chloride and added. At 0° C., a solution of 4.31 g of iodotrimethylsilane in 10 ml of methylene chloride was added. The mixture was warmed to 25° C. and stirred for 15 h. It was then hydrolyzed with 10% strength $Na_2CO_3$ solution.

The phases were separated and the organic phase is analyzed by HPLC.

The HPLC showed no 2,6-diaminopurine and 58.2% cis- and 28.0% trans-(2R)-2-isobutyryloxymethyl-4-(2,6-diaminopurin-9-yl)-1,3-dioxolane.

Example 9

The procedure was analogous to Example 8 but using 3.40 g of (2R-4 $\Xi$)-4-acetoxy-2-isobutyryloxymethyl-1,3-dioxolane with a content of 58.9% (9.0% tert-butyl acetoacetate and 8.7% tert-butyl 2-acetylacetoacetate; this corresponds to 0.40 mol of 1,3-dicarbonyl compound per mole of dioxolane) with the difference that 0.5 mol eq of methyl acetoacetate was added instead of tert-butyl acetoacetate.

HPLC showed no 2,6-diaminopurine and 59.5% cis- and 27.1% trans-(2R)-2-isobutyryloxymethyl-4-(2,6-diaminopurin-9-yl)-1,3-dioxolane.

Example 10

The procedure was analogous to Example 9 with the difference that no further addition of a 1,3-dicarbonyl compound was made (i.e. only the proportion of 0.4 mol of 1,3-dicarbonyl compound derived from the precursor per mole of dioxolane is present).

HPLC showed 8.9% 2,6-diaminopurine and 45.9% cis- and 28.8% trans-(2R)-2-isobutyryloxymethyl-4-(2,6-diaminopurin-9-yl)-1,3-dioxolane.

Example 11

The procedure was analogous to Example 4 but using 49.3 g of (2R-4 $\Xi$)-4-acetoxy-2-isobutyryloxymethyl-1,3-dioxolane with a content of 58.9% (9.0% tert-butyl acetoacetate and 8.7% tert-butyl 2-acetylacetoacetate; this corresponds to 0.40 mol of 1,3-dicarbonyl compound per mole of dioxolane) with the difference that 0.5 mol eq of acetylacetone were added instead of tert-butyl acetoacetate.

HPLC analysis of the crude product showed 57.1% cis-(2R)-2-isobutyryloxymethyl-4-(2,6-diaminopurin-9-yl)-1,3-dioxolane and 27.1% trans-(2R)-2-isobutyryloxymethyl-4-(2,6-diaminopurin-9-yl)-1,3-dioxolane (isomer ratio 2.1:1; HPLC area %).

Crystallization from isopropanol resulted in 17.7 g of colorless crystals which, according to NMR analysis, comprised 1 mol of isopropanol in addition to (2R)-2-isobutyryloxymethyl-4-(2,6-diaminopurin-9-yl)-1,3-dioxolane. The contents by HPLC were 97.5% cis- and 2.2% trans-(2R)-2-isobutyryloxymethyl-4-(2,6-diaminopurin-9-yl)-1,3-dioxolane. This corresponds to a yield of 36.1% of cis isomer based on (2R-4 $\Xi$)-4-acetoxy-2-isobutyryloxymethyl-1,3-dioxolane.

Recrystallization from isopropanol resulted in a pure cis isomer with a content of 99.8% (recrystallization yield 90%).

TABLE 1

Hilbert-Johnson reaction in the presence of various 1,3-dicarbonyl compounds (all reactions in methylene chloride in the presence of 2.5 mol eq of iodotrimethylsilane):

| Example | TBAA + TBAAA content in dioxolane acetate [mol eq] | Addition | Mol eq | cis isomer [area %] | trans isomer [area %] |
|---|---|---|---|---|---|
| 5 | 0.045 | — | — | 34.2 | 30.4 |
| 6 | 0.045 | TBAA | 0.85 | 67.8 | 31.7 |
| 7 | 0.045 | TMS-TBAA | 0.50 | 62.6 | 33.6 |
| 8 | 0.67 | — | — | 58.2 | 28.0 |
| 9 | 0.40 | ACM | 0.5 | 59.5 | 27.1 |
| 10 | 0.4 | — | — | 45.9 | 28.8 |
| 11 | 0.4 | AcAc | 0.5 | 57.1 | 27.1 |

TBAA = tert-butyl acetoacetate;
TBAAA = tert-butyl 2-acetylacetoacetate
TMS-TBAA = tert-butyl 3-trimethylsilyloxybut-2-enoate

Example 12

The procedure was analogous to Example 8 with the difference that 1,2-dichloroethane was used instead of methylene chloride as solvent.

HPLC showed no 2,6-diaminopurine and 53.1% cis- and 29.9% trans-(2R)-2-isobutyryloxymethyl-4-(2,6-diaminopurin-9-yl)-1,3-dioxolane.

Example 13

The procedure was analogous to Example 8 with the difference that acetonitrile was used instead of methylene chloride as solvent. In the workup, methylene chloride was added in order to extract the product.

HPLC showed no 2,6-diaminopurine and 45.3% cis- and 36.4% trans-(2R)-2-isobutyryloxymethyl-4-(2,6-diaminopurin-9-yl)-1,3-dioxolane.

Example 14

The procedure was analogous to Example 8 with the difference that trimethylsilyl trifluoromethanesulfonate was used instead of iodotrimethylsilane as Lewis acid.

HPLC showed no 2,6-diaminopurine and 33.7% cis- and 47.5% trans-(2R)-2-isobutyryloxymethyl-4-(2,6-diaminopurin-9-yl)-1,3-dioxolane.

Example 15

The procedure was analogous to Example 14 with the difference that 1,2-dichloroethane was used instead of methylene chloride as solvent.

HPLC showed no 2,6-diaminopurine and 31.7% cis- and 40.9% trans-(2R)-2-isobutyryloxymethyl-4-(2,6-diaminopurin-9-yl)-1,3-dioxolane.

TABLE 2

Hilbert-Johnson reaction in various solvents and with various Lewis acids:

| Example | TBAA + TBAAA present in dioxolane acetate [mol eq] | Solvent | Lewis acid [2.5 mol eq] | cis isomer [area %] | trans isomer [area %] |
|---|---|---|---|---|---|
| 12 | 0.67 | 1,2-DCE | TMSI | 53.1 | 29.9 |
| 13 | 0.67 | MeCN | TMSI | 45.3 | 36.4 |
| 14 | 0.67 | $CH_2Cl_2$ | TMSOTf | 33.7 | 47.5 |
| 15 | 0.67 | 1,2-DCE | TMSOTf | 31.7 | 40.9 |

TBAA = tert-butyl acetoacetate;
TBAAA = tert-butyl 2-acetylacetoacetate
1,2-DCE = 1,2-dichloroethane
MeCN = acetonitrile
TMSOTf = trimethylsilyl trifluoromethanesulfonate (trimethylsilyl triflate)

Example 16

Preparation of cis- and trans-(2R)-2-isobutyryloxymethyl-4-(2,6-diaminopurin-9-yl)-1,3-dioxolane

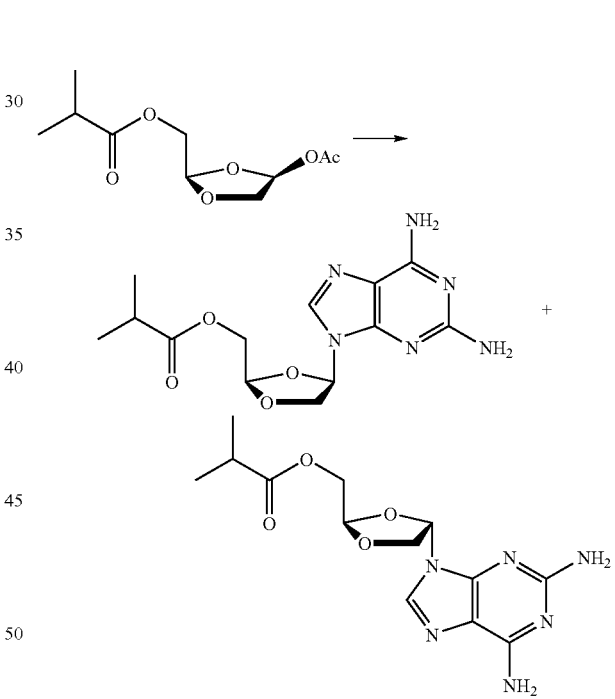

48.0 g of (2R-4 Ξ)-4-acetoxy-2-isobutyryloxymethyl-1,3-dioxolane with a content of 60.5% (9.0% tert-butyl acetoacetate and 3.1% tert-butyl 2-acetylacetoacetate; this corresponds to 0.28 mol of 1,3-dicarbonyl compound per mole of dioxolane) were introduced into 520 ml of methylene chloride. 14.8 g of tert-butyl acetoacetate and 179.8 g of 0.8 molal solution of tris(trimethylsilyl)-2,6-diaminopurine in methylene chloride (from Example 1) were added. The solution was cooled to 0° C. and, at this temperature, a solution of 62.6 g of iodotrimethylsilane (content 98%) in 125 ml of methylene chloride was added dropwise over the course of 20 min. The mixture was then stirred at 0 to 10° C. for 20 h.

The reaction mixture was added dropwise to a solution of 34.2 g of 20% strength hydrochloric acid in 725 g of water at 0 to 10° C. The mixture was warmed to 25° C. and stirred for 15 min.

The phases were separated and the organic phase was back-extracted once with 125 ml of 0.5 N hydrochloric acid. The combined aqueous phases were washed twice with 100 ml of methylene chloride each time. Then, after addition of a further 474 ml of methylene chloride, the pH was adjusted to 9.0 by adding 700 g of a 10% strength sodium carbonate solution.

The mixture was stirred at 25° C. for 1 h, and the phases were separated. The aqueous phase was back-extracted twice with 123 ml of methylene chloride each time, and the combined organic phases were washed once with 200 ml of water.

Removal of the solvent in vacuo resulted in 27.6 g of yellowish solid.

HPLC analysis showed 71.2% cis-(2R)-2-isobutyryloxymethyl-4-(2,6-diaminopurin-9-yl)-1,3-dioxolan and 26.5% trans-(2R)-2-isobutyryloxymethyl-4-(2,6-diaminopurin-9-yl)-1,3-dioxolane (isomer ratio 2.7:1; HPLC area %; crude yield 49%).

The crude product was recrystallized from isopropanol. 16.2 g of colorless crystals were obtained and contained, according to NMR analysis, 1 mol of isopropanol in addition to (2R)-2-isobutyryloxymethyl-4-(2,6-diaminopurin-9-yl)-1,3-dioxolane. The contents according to HPLC were 99.0% cis- and 0.9% trans-(2R)-2-isobutyryloxymethyl-4-(2,6-diaminopurin-9-yl)-1,3-dioxolane. This corresponds to a yield of 33.3% of cis isomer based on (2R-4 Ξ)-4-acetoxy-2-isobutyryloxymethyl-1,3-dioxolane.

Example 17

Preparation of (2R-4 Ξ)-4-acetoxy-2-tert-butyldiphenylsilyloxymethyl-1,3-dioxolane

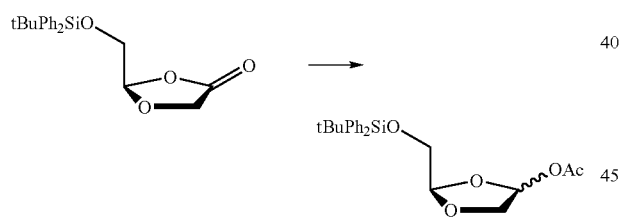

98.4 g of LiAlH(OtBu)₃ and 964 g of THF were introduced into a dry flask and cooled to −10° C. 98.5 g of (2R)-2-tert-butyldiphenylsilyloxymethyl-1,3-dioxolan-4-one were added dropwise over the course of 45 min. The mixture was warmed to 25° C., 33.7 g of 4-dimethylaminopyridine were added, and the mixture was stirred for 1 h. It was again cooled to −10° C. and then 209 g of acetic anhydride were added dropwise at this temperature. The mixture was stirred at −10 to 0° C. for 15 h.

It was then quenched by adding 415 g of 15% strength NH₄Cl solution and diluted with 400 g of water. The THF was substantially removed by distillation in vacuo and then 480 g of ethyl acetate were added. The mixture was thoroughly shaken and the phases were separated. The aqueous phase was back-extracted once with ethyl acetate, and the combined organic phases were washed with water and NaHCO₃ solution. The solvent was distilled off in vacuo, and the product was obtained as an orange-colored oil (yield 110.7 g with 70% content corresponding to 70% of theory).

Example 18

Preparation of cis- and trans-(2R)-2-tert-butyldiphenylsilyloxymethyl-4-(2,6-diaminopurin-9-yl)-1,3-dioxolane

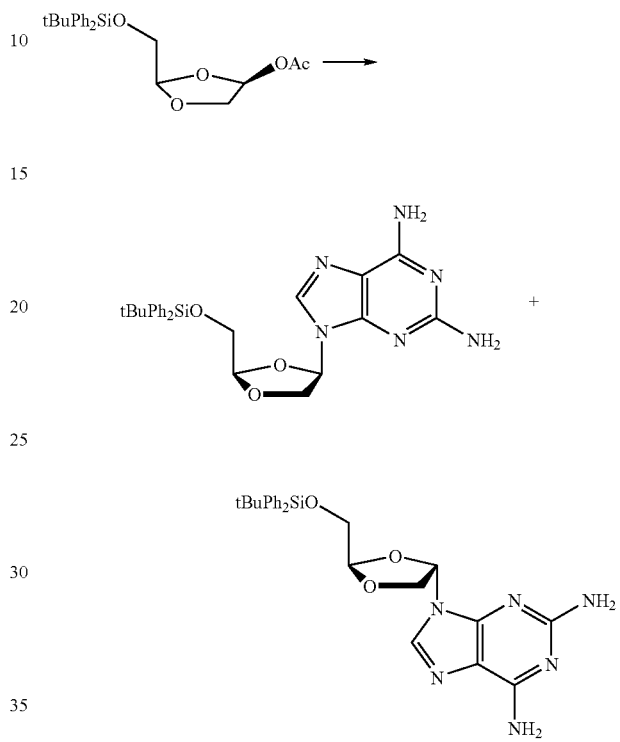

27.5 g of (2R-4 Ξ)-4-acetoxy-2-tert-butyldiphenylsilyloxymethyl-1,3-dioxolane with a content of 70.0% (11.2% tert-butyl acetoacetate and 5.3% tert-butyl 2-acetylacetoacetate; this corresponds to 0.50 mol of 1,3-dicarbonyl compound per mole of dioxolane) were introduced into 96 ml of methylene chloride. A solution of 5.4 g of tert-butyl acetoacetate in 21 ml of methylene chloride and 50 ml of a 1.0 molar solution of tris(trimethylsilyl)-2,6-diaminopurine in methylene chloride (see Example 1) were likewise added. The solution was cooled to 0° C. and, at this temperature, a solution of 22.6 g of iodotrimethylsilane (content 95.8%) in 45 ml of methylene chloride was added dropwise over the course of 20 min. The mixture was then stirred at 0° C. for 1 h, warmed to 25° C. and stirred at this temperature for 15 h. It was quenched by adding 250 ml of a 10% strength Na₂CO₃ solution and stirred for 10 min. The phases were separated and the aqueous phase was back-extracted twice with methylene chloride. The combined organic phases were washed with 10% strength Na₂CO₃ solution and water and filtered through kieselguhr. The solvent was removed in vacuo to result in 13.5 g of yellowish solid.

HPLC analysis of the product showed 65.8% cis-(2R)-2-tert-butyldiphenylsilyloxymethyl-4-(2,6-diaminopurin-9-yl)-1,3-dioxolane and 33.4% trans-(2R)-2-tert-butyldiphenylsilyloxymethyl-4-(2,6-diaminopurin-9-yl)-1,3-dioxolane (isomer ratio 2.0:1; HPLC area %). This corresponds to a yield of cis isomer of 40%.

Example 19

Preparation of [(2R,4R)-[4-(2,6-diamino-9H-purin-9-yl)-1,3-dioxolan-2-yl]methanol [(−)-DAPD]

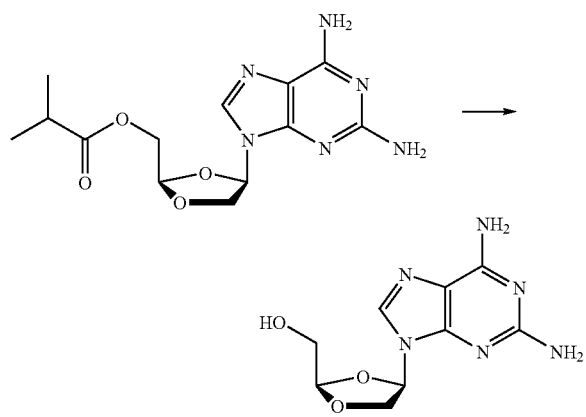

31.05 g of (2R,4R)-2-isobutyryloxymethyl-4-(2,6-diaminopurin-9-yl)-1,3-dioxane×2-propanol (cf. Example 4) were dissolved in 310 ml of NH$_3$-saturated methanol. The solution was stirred at 25° C. for 15 h, and the solvent was distilled off in vacuo. The residue was recrystallized from ethanol/water. 17.10 g (83%) of (−)-DAPD were obtained as colorless crystals.

$^1$H NMR (360 MHz, DMSO-d$_6$): δ=3.61 (dd, J$_1$=6.0 Hz, J$_2$=3.2 Hz; CH$_2$OH); 4.20 (dd, J$_1$=9.5 Hz, J$_2$=5.5 Hz; 1H—C(5')); 4.45 (dd, J$_1$=9.5 Hz, J$_2$=1.8 Hz; 1H—C(5')); 5.05 (Ψt, J=3.2 Hz; 1H—C(2')); 5.15 (Ψt, J=6.0 Hz; CH$_2$OH); 5.83 (s; 2H—NH$_2$); 6.21 (dd, J$_1$=5.5 Hz, J$_2$=1.8 Hz; 1H—C(4')); 5.83 (s; 2H—NH$_2$); 7.87 (s; 1H—C(8)).

The invention claimed is:

1. A method for the production of compounds of the formula (1)

where R$^1$ is a hydroxyl protective group and R$^8$, R$^9$, R$^{10}$, R$^{11}$ are, independently of one another, hydrogen or an amino protective group; by reacting a compound of the formula (2)

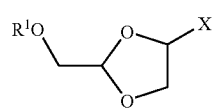

where X is a leaving group, with a 2,6-diaminopurine derivative of the formula (5)

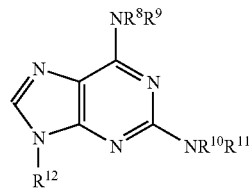

where R$^{12}$ is a silyl radical —SiR$^4$R$^5$R$^6$ where R$^4$, R$^5$, and R$^6$ are each independently an aliphatic or aromatic radical containing up to 20 carbon atoms, in the presence of a Lewis acid, wherein a 1,3-dicarbonyl compound or an —SiR$^4$R$^5$R$^6$ silylated derivative of a 1,3-dicarbonyl compound is present during at least a portion of the reaction, and wherein the 1,3-dicarbonyl compound has the following formula:

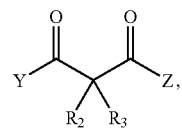

where Y and Z are, independently of one another, hydrogen, an alkyl radical having from 1 to 20 C atoms, an aryl radical having from 6 to 20 C atoms or an alkyloxy group having from 1 to 20 C atoms and R$^2$ and R$^3$, are, independently of one another, hydrogen, an acyl radical of an aromatic or aliphatic carboxylic acid having from 2 to 20 C atoms, an alkyl radical having from 1 to 20 C atoms or an aryl radical having from 6 to 20 C atoms, and at least one of R$^2$ and R$^3$ H.

2. The method of claim 1, wherein the compounds of the formula (1) are obtained in an optical configuration of the formulae (1a), (1b), (1c) or (1d)

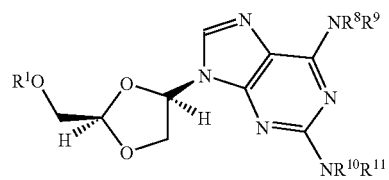

Formula (1a)

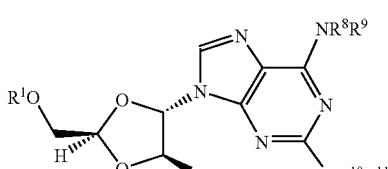

Formula (1b)

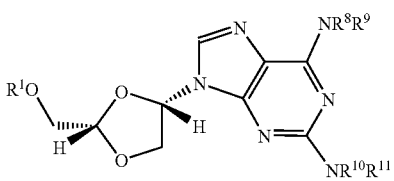

Formula (1c)

Formula (1d)

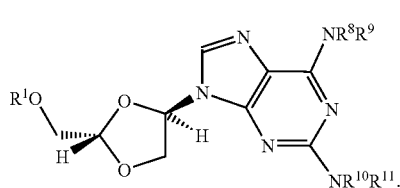

3. The method of claim 1, wherein $R^1$ is selected from the group consisting of acyl, alkyl, alkoxyalkyl, arylalkyl, arylalkoxyalkyl, and —$SiR^4R^5R^6$ silyl radicals.

4. The method of claim 1, wherein X is selected from the group consisting of halogen, acyloxyl, alkylsulfonyloxyl, arylsulfonyloxyl, alkoxyl and aryloxl radicals.

5. The method of claim 1, wherein at least one compound selected from the group consisting of trialkylsilylhalides and trialkylsilyl perfluroalkanesulfonates is used as Lewis acid.

6. The method of claim 1, wherein the silylated derivative of a 1,3-dicarbonyl compound is a silyl derivative of a β-carbonyl carboxylic ester, of a 1,3-diketone, or of a malonic acid derivative of the formula (4)

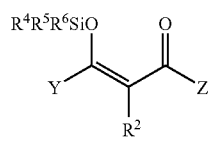

where Y and Z are, independently of one another, hydrogen, an alkyl radical having from 1 to 20 C atoms, an aryl radical having from 6 to 20 C atoms or an alkyloxy group having from 1 to 20 C atoms and $R^2$ and $R^3$, are, independently of one another, hydrogen, an acyl radical of an aromatic or aliphatic carboxylic acid having from 2 to 20 C atoms, an alkyl radical having from 1 to 20 C atoms or an aryl radical having from 6 to 20 C atoms. $R^4$, $R^5$ and $R^6$ are independently of one another, an aliphatic or aromatic radical having from 1 to 20 C atoms.

7. The method of claim 1, wherein at least one amino protective group is selected from the group consisting of acyl radicals, acyloxycarbonyl radicals, alkyl radicals, arylalkyl radicals, and —$SiR^4R^5R^6$ silyl radicals.

8. The method of claim 1, wherein resulting compounds of the formula (1) are subsequently purified by recrystallization.

9. The method of claim 1, further comprising removing protective group $R^1$, as well as any of $R^8$-$R^{11}$ that were amino protective groups, to form a compound of the formula (6)

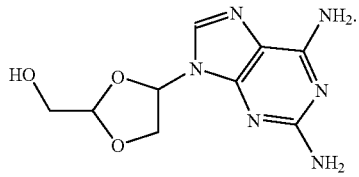

10. The method of claim 1, wherein $R^4$, $R^5$, and $R^6$ are each independently selected from the group consisting of $C_{1-20}$ alkyl.

11. The method of claim 1, wherein $R^4$, $R^5$, and $R^6$ are each independently selected from the group consisting of $C_{1-10}$ alkyl.

12. The method of claim 1, wherein $R^4$, $R^5$, and $R^6$ are each independently selected from the group consisting of $C_{1-10}$ alkyl and phenyl.

13. The method of claim 1, wherein each of $R^4$, $R^5$, and $R^6$ is methyl.

14. The method of claim 1, wherein at least one silyl group —$SiR^4R^5R^6$ is selected from the group consisting of trimethylsilyl, triethylsilyl, tripropylsilyl, tert-butyldimethylsilyl, and ter-butyldiphenylsilyl.

15. The method of claim 1, wherein X is selected from the group consisting of halogen, acyloxy, alkylsulfonyloxyl, and arylsulfonyloxyl radicals.

16. The method of claim 1, wherein X is selected from the group consisting of alkoxyl radicals.

17. The method of claim 1, wherein at least one amino protective group is selected from the group consisting of acyl radicals, acyloxycarbonyl radicals, arylalkyl radicals, and —$SiR^4R^5R^6$ silyl radicals.

18. The method of claim 1, wherein:
a) the 1,3-dicarbonyl compound is selected from the group consisting of methyl acetoacetate, ethyl acetoacetate, tert-butyl acetoacetate, isobutyl acetoacetate, isopropyl acetoacetate, n-propyl acetoacetate, benzyl acetoacetate, methyl 2-acetylacetoacetate, ethyl 2-acetylacetoacetate, tert-butyl 2-acetylacetoacetate, methyl 3-oxopentanoate, ethyl 3-oxopentanoate, tert-butyl 3-oxopentanoate, methyl 3-oxohexanoate, ethyl 3-oxohexanoate, acetylacetone, 2,4-hexanedione, 3,5-heptanedione, dimethyl malonate, diethyl malonate, diisobutyl malonate, diisopropyl malonate and di-tert-butyl malonate, or b) the —$SiR^4R^5R^6$ silylated derivative of the 1,3-dicarbonyl compound is selected from the group consisting of methyl 3-trimethylsilyloxyacrylate, ethyl 3-trimethylsilyloxyacrylate, 4-trimethylsilyloxypent-3-en-2-one, 4-triethylsilyloxypent-3-en-2-one, 4-(tert-butyldimethylsilyloxy)pent-3-en-2-one, 4-(tert-butyl-diphenylsilyloxy)pent -3-en-2-one, methyl 3-trimethyl-silyloxybut-2-enoate, ethyl 3-trimethylsilyloxybut-2-enoate, tert-butyl 3-trimethylsilyloxybut-2-enoate, methyl 3-trimethylsilyloxybut-2-enoate, ethyl 3-trimethylsilyloxybut-2-enoate and tert-butyl 3-trimethylsilyloxybut-2-enoate.

\* \* \* \* \*